(12) United States Patent
Janak

(10) Patent No.: US 8,808,500 B2
(45) Date of Patent: Aug. 19, 2014

(54) METHOD FOR THE USE OF OXIDANTS FOR MICROBIAL CONTROL UNDER REDUCING CONDITIONS

(75) Inventor: Kevin Janak, Ossining, NY (US)

(73) Assignee: Lonza Inc., Allendale, NJ (US)

( * ) Notice: Subject to any disclaimer, the term of this patent is extended or adjusted under 35 U.S.C. 154(b) by 0 days.

(21) Appl. No.: 13/981,211

(22) PCT Filed: Jan. 20, 2012

(86) PCT No.: PCT/EP2012/050856
§ 371 (c)(1),
(2), (4) Date: Jul. 23, 2013

(87) PCT Pub. No.: WO2012/101051
PCT Pub. Date: Aug. 2, 2012

(65) Prior Publication Data
US 2013/0302443 A1    Nov. 14, 2013

Related U.S. Application Data

(60) Provisional application No. 61/435,536, filed on Jan. 24, 2011.

(51) Int. Cl.
*D21H 21/36*   (2006.01)
*A01N 59/08*   (2006.01)
*A01N 35/02*   (2006.01)
*A01N 25/22*   (2006.01)

(52) U.S. Cl.
USPC ............... 162/73; 162/70; 162/87; 162/158; 162/161; 162/182; 162/185; 424/657; 424/661

(58) Field of Classification Search
USPC ......... 162/70, 72–74, 87, 88, 1, 58, 160, 161, 162/164.1, 182, 164.6, 185; 424/600, 657, 424/661, 667, 673
See application file for complete search history.

(56) References Cited

U.S. PATENT DOCUMENTS

| | | | |
|---|---|---|---|
| 5,139,613 A | 8/1992 | LaChapelle | |
| 5,360,551 A * | 11/1994 | Weber | 210/719 |
| 6,319,356 B1 | 11/2001 | Durkes et al. | |
| 6,440,689 B1 * | 8/2002 | Banks et al. | 435/29 |
| 6,482,756 B2 * | 11/2002 | Li | 442/123 |
| 7,837,883 B2 * | 11/2010 | Barak | 210/756 |
| 2003/0207884 A1 | 11/2003 | Haap et al. | |
| 2009/0314445 A1 | 12/2009 | Shevchenko et al. | |

FOREIGN PATENT DOCUMENTS

| | | |
|---|---|---|
| DE | 102007028923 | 12/2008 |
| GB | 2138799 | 10/1984 |
| GB | 2333772 | 8/1999 |
| WO | WO03/016556 | 2/2003 |

* cited by examiner

*Primary Examiner* — Dennis Cordray
(74) *Attorney, Agent, or Firm* — Dority & Manning, P.A.

(57) ABSTRACT

Microbial growth in an aqueous system containing borohydride residues is controlled by adding an aldehyde or aldehyde source, followed by adding an active halogen biocide. The active halogen biocide is preferably stabilized by an N-hydrogen compound.

24 Claims, No Drawings

METHOD FOR THE USE OF OXIDANTS FOR MICROBIAL CONTROL UNDER REDUCING CONDITIONS

CROSS REFERENCE TO RELATED APPLICATION

This application is the national stage entry of International Patent Application No. PCT/EP2012/050856 having a filing date of Jan. 20, 2012, which claims the filing benefit of U.S. Provisional Application No. 61/435,536 having a filing date of Jan. 24, 2011 and which are both incorporated herein by reference.

The invention relates to a method for controlling microbial growth in aqueous systems containing borohydride, such as solutions or suspensions obtained after application of borohydride-based reducing bleaches. It further relates to a method for stabilizing active halogen biocides in aqueous systems with reducing conditions.

The oxidizing or reducing power of a chemical substance or composition is commonly quantified by its oxidation-reduction ("redox") potential (ORP). The lower (i.e., the more negative) the ORP of a substance or composition, the more powerful is its reducing effect.

Reducing bleaches are frequently used in paper making applications. One such type of bleaching processes employs borohydride ($BH_4^-$) chemistry. While enhancing paper brightness, the use of such solutions can also result in borohydride residues in the produced pulp. These residues result in providing extremely reducing conditions (ORP as low as −500 to −600 mV). Borohydride residues make pulp preservation and subsequent paper machine deposit control more difficult as many major paper slimicides and preservatives such as dibromonitrilopropionamide, isothiazolinones, and, in particular, oxidizing biocides are unstable in the presence of borohydride.

Surprisingly, it has been found that via the use of an aldehyde or aldehyde source, application of oxidizing biocides to systems containing residual borohydride under reducing conditions (negative ORP) is possible and can provide both a residual halogen and microbial control even under such conditions.

The neutralization of halogen under reducing conditions is well known and often precludes proper system control via standard methods such as ORP controllers or titrimetric analytical methods. It has been found that the use of an aldehyde or aldehyde source to bring the ORP to a level greater than approximately −350 mV allows for normally incompatible reducing agents and oxidant materials to coexist for time periods sufficient for microbial control applications and analysis via standard N,N-diethyl-p-phenylendiamine (DPD) titrimetric analytical methods.

According to the invention, microbial growth in an aqueous system containing borohydride residues is controlled by adjusting and maintaining an ORP>−350 mV, preferably >−300 mV, and more preferably >−250 mV, via the contact of an aldehyde or aldehyde source with the borohydride-containing aqueous system for a period of time prior to introduction of the oxidant to the aqueous system, followed by addition of an oxidant chemical, such as sodium hypochlorite, a stabilized oxidant such as bromochlorodimethylhydantoin, or a combination of an oxidant chemical and a stabilizer chemical, such as sodium hypochlorite in combination with 5,5-dimethylhydantoin.

Herein, an aldehyde source (or aldehyde donor) is a compound that is able to release, or to break down into, one or more molecules of an aldehyde. The molar ratios given below relate to the amount of aldehyde present or produced or, for aldehydes having two or more aldehyde groups, such as glyoxal or glutaraldehyde, to the equivalent amount of monovalent aldehyde.

Preferred aldehyde and aldehyde sources include dimethyloldimethylhydantoin, glutaraldehyde, triazines, hexamethylene tetramine, formaldehyde, glyoxal, bis(tetrakishydroxymethylphosphonium) sulfate, acetals, such as dimethoxymethane, and mixtures of the aforementioned.

Preferred oxidants or oxidant mixtures include halogen sources such as sodium hypochlorite, sodium hypochlorite and sodium bromide, bromochlorohydantoins, dibromohydantoins, dichlorohydantoins. In a preferred embodiment the source of active halogen source is selected from the group consisting of elemental chlorine, elemental bromine, bromine chloride, an alkali metal hypohalite, an alkaline earth metal hypohalite, a mono- and/or dihalogenated hydantoin, a halogenated cyanurate, a halogenated cyanuric acid, and mixtures of the aforementioned among each other and/or with sodium bromide. Most preferably the source of active halogen source is an alkali metal hypohalite, in particular sodium hypochlorite.

The oxidant or oxidant mixtures may be combined with a solution or composition containing at least one halogen stabilizing compound, such as optionally substituted N-hydrogen compounds. Specifically, compositions comprising at least one N-hydrogen compound selected from the group consisting of p-toluenesulfonamide, 5,5-dialkylhydantoins, methanesulfonamide, barbituric acid, 5-methyluracil, imidazoline, pyrrolidone, morpholine, acetanilide, acetamide, N-ethylacetamide, phthalimide, benzamide, succinimide, N-methylolurea, N-methylurea, acetylurea, methyl allophanate, methyl carbamate, phthalohydrazide, pyrrole, indole, formamide, N-methylformamide, dicyanodiamide, ethyl carbamate, 1,3-dimethylbiuret, methylphenylbiuret, 4,4-dimethyl2-oxazolidinone, 6-methyluracil, 2-imidazolidinone, ethyleneurea, 2-pyrimidone, azetidin-2-one, 2-pyrrolidone, caprolactam, phenylsulfinimide, phenylsulfinimidylamide, diaryl- or dialkylsulfinimides, isothiazoline-1,1-dioxide, hydantoin, glycine, piperidine, piperazine, ethanolamine, glycinamide, creatine, glycoluril, ammonia, ammonium salts, and urea.

Preferred ammonium salts include ammonium halides, such as ammonium fluoride, ammonium chloride, ammonium bromide or ammonium iodide, ammonium sulfate, ammonium hydrogensulfate, ammonium bicarbonate, ammonium carbonate, ammonium carbamate, ammonium alkanesulfonates, such as ammonium methanesulfonate, ammonium alkylsulfates, and ammonium carboxylates, such as ammonium formate and ammonium acetate, and mixtures of the aforementioned.

Throughout this specification, relative quantities are sometimes defined by ranges, and by lower and upper boundaries of ranges. Each lower boundary can be combined with each upper boundary to define a range. The lower and upper boundaries should each be taken as a separate element.

The above compositions comprising at least one N-hydrogen compound can effectively stabilize a source of active halogen in aqueous solution under reducing conditions.

The molar ratio of borohydride to aldehyde compound is preferably from 2:1 to 1:20, more preferably 1:1 to 1:15, and most preferred 1:2 to 1:10.

The molar ratio of active halogen to additional N-hydrogen compound is preferably in the range of 20:1 to 0.1:1, preferably in the range of 10:1 to 0.2:1, most preferably in the range of 5:1 to 2:1.

The above compositions are expediently used in aqueous solutions having a pH in the range of 3 to 11, preferably in the range of 5 to 10, and more preferably in the range of 7 to 9.5.

For stabilizing a source of active halogen in aqueous solution, said source of active halogen in aqueous solution can be mixed with the above compositions.

Alternatively, a source of active halogen in aqueous solution can be stabilized by admixing it with the aforementioned aqueous solution comprising the above composition.

Applications which may benefit from the use of oxidants and stabilized oxidants under reducing conditions according to the invention include pulp and papermaking, recycle paper pulping and papermaking, pulp or biomass bleaching, textile bleaching, and similar applications.

In a preferred embodiment the concentration of active halogen (as $Cl_2$) stabilized by an N-hydrogen compound is 0.1 to 20 ppm. Here and herein below, the expression "as $Cl_2$" denotes the concentration of elemental chlorine that is stoichiometrically equivalent to the concentration of active halogen in a given system.

Preferred aqueous systems are pulp and papermaking slurries and liquors, recycle pulp slurries, pulp thick stock, deinking pulp slurries, pulp or biomass bleaching slurries and liquids, textile bleaching liquids and clay slurries.

According to the invention, optimized cost performance for microbial control can be achieved through the ability to use oxidants under reducing conditions via application of aldehyde compounds for brief periods prior to co-application with active halogens. The use of oxidants under reducing conditions has been prohibited to date by the rapid neutralization of oxidant under these conditions and the inability to monitor residual oxidant in the system. The current invention provides methodologies for utilizing these classes of compounds cooperatively.

The following non-limiting examples are intended to illustrate the invention in more detail.

EXAMPLES

The expression "CFU/mL" denotes the colony-forming units per milliliter. Unless otherwise indicated all concentrations in percent or ppm are expressed on a weight basis.

Aqueous solutions containing sodium borohydride were mixed at 21° C. to obtain a solution having an initial borohydride content (as $NaBH_4$) of 30-50 ppm, an alkalinity (as $CaCO_3$) of 400 ppm, and a pH of 8.5-9.5. The temperature of the solution was maintained at 21° C. and the ORP of the solution was measured at specified time intervals. The procedure consisted of adding a known amount of aldehyde donor, such as dimethyloldimethylhydantoin or glyoxal, to the samples at a known molar ratio with respect to the borohydride content and following the time-dependence of the ORP.

In order to demonstrate the compatibility of oxidants under reducing conditions, sodium hypochlorite was combined with an N-hydrogen compound, such as 5,5-dimethylhydantoin, and added to solutions as described above at different intervals and, consequently, different ORP values. The remaining halogen concentration was then measured by standard DPD total halogen methodologies over time.

Example 1

The ability of aldehyde donors to attenuate the ORP of borohydride reductive bleaching waters is demonstrated in Table 1, which reveals that an increase in ORP results over time upon addition of aldehyde donor.

TABLE 1

| Time (min) | Untreated Control ORP (mV) | Treated Sample ORP (mV) | % Increase Due to Treatment |
|---|---|---|---|
| 0 | −602 | −618 | −2.7% |
| 2.5 | −610 | −562 | 7.9% |
| 25 | −570 | −493 | 13.5% |
| 30 | −572 | −450 | 21.3% |
| 40 | −520 | −353 | 32.1% |

Example 2

In order to demonstrate the effectiveness of the method of the present invention at stabilizing halogen oxidants even under reducing conditions (negative ORP), sodium hypochlorite was added to a sodium borohydride solution prepared in the manner above to solutions treated with dimethyloldimethylhydantoin and the residual total halogen (as $Cl_2$) was analyzed. For comparison, the residual total halogen (as $Cl_2$) was analyzed without the use of dimethyloldimethylhydantoin.

TABLE 2

| Time After Addition (min) | ORP (mV) - DMDMH treated | Total Halogen (ppm as $Cl_2$) with DMDMH | Total Halogen (ppm as $Cl_2$) without DMDMH |
|---|---|---|---|
| 2 | −251 | 1.59 | <0.1 |
| 43 | −77 | 1.33 | <0.1 |

Example 3

The ability of stabilized oxidants to exhibit biocidal performance upon release of halogen even under reducing conditions was investigated. $NaBH_4$ was added to the process water from a North American paper mill targeting a residual borohydride content of 35 ppm as $NaBH_4$. An untreated control, borohydride treated control, aldehyde treated sample, and aldehyde+stabilized halogen treated sample (target 2 ppm total $Cl_2$ dose) were tested. The initial and final ORP after 3 h at 37° C. were measured, as well as the residual halogen present after 3 h. The microbial population was that provided by the pulp slurry 24-48 h prior to testing and storing at 37° C., thus allowing microbial growth to a high test level.

Microbial populations were analyzed using SaniCheck dip slides from Biosan Laboratories, Inc., Warren Mich. Populations reported are total aerobic counts rounded to the nearest power of 10 via comparison to standard charts. The test results are shown in Table 3.

TABLE 3

| | Untreated Control | | Borohydride Treated Control | | Borohydride + 140 ppm Aldehyde Donor | | Borohydride + 140 ppm Aldehyde Donor + 2 ppm Stabilized Halogen | | |
|---|---|---|---|---|---|---|---|---|---|
| Contact Time (h) | Microbial Counts (CFU/mL) | ORP (mV) | Microbial Counts (CFU/mL) | ORP (mV) | Microbial Counts (CFU/mL) | ORP (mV) | Microbial Counts (CFU/mL) | ORP (mV) | Total Halogen (ppm as $Cl_2$) |
| 3 | $1 \times 10^5$ | 165 | $1 \times 10^6$ | −420 | $1 \times 10^5$ | −350 | $1 \times 10^3$ | −350 | 0.72 |

The above example demonstrates that the presence of the aldehyde donor increases the ORP and that halogen stabilization at negative ORP values provides a method by which oxidants can exhibit microbial control without immediate neutralization under reducing conditions.

The invention claimed is:

1. A method for controlling microbial growth in an aqueous system containing borohydride residues, said method comprises adding an aldehyde or an aldehyde source to said aqueous system, followed by adding an oxidant, said oxidant being a source of active halogen, such that a residual oxidant level under reducing conditions is provided.

2. The method of claim 1, wherein the aldehyde or aldehyde source is added in an amount sufficient to achieve an ORP of greater than −350 mV.

3. The method of claim 2, wherein the aldehyde or aldehyde source is added in an amount sufficient to achieve an ORP of greater than −300 mV.

4. The method of claim 3, wherein the aldehyde or aldehyde source is added in an amount sufficient to achieve an ORP of greater than −250 mV.

5. The method of claim 1, wherein the aldehyde or aldehyde source is selected from the group consisting of dimethyloldimethylhydantoin, glutaraldehyde, triazines, hexamethylenetetramine, formaldehyde, 4,4-dimethyloxazolidine, tetrahydro-3,5-di-methyl-2H-1,3,5-thiadiazine-2-thione, glyoxal, bis(tetrakishydroxymethylphosphonium) sulfate, acetals, and mixtures of the aforementioned.

6. The method of claim 1, wherein the source of active halogen is selected from the group consisting of elemental chlorine, elemental bromine, bromine chlorides, alkali metal hypohalites, alkaline earth metal hypohalites, alkali or alkaline earth metal hypochlorites combined with bromides, monohalogenated hydantoins, dihalogenated hydantoins, halogenated cyanurates, halogenated cyanuric acids, and mixtures of the aforementioned.

7. The method of claim 6, wherein the source of active halogen is selected from the group consisting of bromochlorohydantoins, dibromohydantoins, dichlorohydantoins, and mixtures of the aforementioned.

8. The method of claim 6, wherein the source of active halogen is selected from the group consisting of sodium hypochlorite and sodium hypochlorite/sodium bromide.

9. The method of claim 1, wherein the source of active halogen is combined with a solution or composition comprising at least one halogen stabilizing compound.

10. The method of claim 9, wherein the at least one halogen stabilizing compound is an N-hydrogen compound selected from the group consisting of p-toluenesulfonamide, 5,5-dialkylhydantoins, methanesulfonamide, barbituric acid, 5-methyluracil, imidazoline, pyrrolidone, morpholine, acetanilide, acetamide, N-ethylacetamide, phthalimide, benzamide, succinimide, N-methylolurea, N-methylurea, acetylurea, methyl allophanate, methyl carbamate, phthalohydrazide, pyrrole, indole, formamide, N-methylformamide, dicyanodiamide, ethyl carbamate, 1,3-dimethylbiuret, methylphenylbiuret, 4,4-dimethyl-2-oxazolidinone, 6-methyluracil, 2-imidazolidinone, ethyleneurea, 2-pyrimidone, azetidin-2-one, 2-pyrolidone, caprolactam, phenylsulfinimide, phenylsulfinimidylamide, diarylsulfinimides, dialkylsulfinimides, isothiazoline-1,1-dioxide, hydantoin, glycine, piperidine, piperazine, ethanolamine, glycinamide, creatine, glycoluril, ammonia, ammonium salts, and urea.

11. The method of claim 10, wherein the at least one halogen stabilizing compound is an ammonium salt selected from the group consisting of ammonium halides, ammonium sulfate, ammonium hydrogensulfate, ammonium bicarbonate, ammonium carbonate, ammonium carbamate, ammonium alkanesulfonates, ammonium alkylsulfates, and ammonium carboxylates, and mixtures of the aforementioned.

12. The method of claim 1, wherein the molar ratio of borohydride to aldehyde or aldehyde source is from 2:1 to 1:20.

13. The method of claim 12, wherein the molar ratio of borohydride to aldehyde or aldehyde source is from 1:1 to 1:15.

14. The method of claim 13, wherein the molar ratio of borohydride to aldehyde or aldehyde source is from 1:2 to 1:10.

15. The method of claim 10, wherein the molar ratio of active halogen to additional N-hydrogen compound is in the range of 20:1 to 0.1:1.

16. The method of claim 15, wherein molar ratio of active halogen to additional N-hydrogen compound is in the range of 10:1 to 0.2:1.

17. The method of claim 16, wherein molar ratio of active halogen to additional N-hydrogen compound is in the range of 5:1 to 2:1.

18. The method of claim 10, wherein the solution or composition comprising at least one halogen stabilizing compound is an aqueous solution having a pH in the range of 3 to 11.

19. The method of claim 18, wherein the solution or composition comprising at least one halogen stabilizing compound is an aqueous solution having a pH in the range of 5 to 10.

20. The method of claim 19, wherein the solution or composition comprising at least one halogen stabilizing compound is an aqueous solution having a pH in the range of 7 to 9.5.

21. The method of claim 10, wherein the source of active halogen is in an aqueous solution and is admixed with the composition comprising the at least one halogen stabilizing compound.

22. The method of claim 10, wherein the source of active halogen is in an aqueous solution and is admixed with an aqueous solution comprising the composition comprising the at least one halogen stabilizing compound.

23. The method of claim 10, wherein the concentration of active halogen (as $Cl_2$) stabilized by the at least one halogen stabilizing compound is 0.1 to 20 ppm in the aqueous system.

24. The method of claim 1, wherein the aqueous system is selected from the group consisting of pulp and papermaking slurries and liquors, recycle pulp slurries, pulp thick stock, deinking pulp slurries, pulp bleaching slurries and liquids, biomass bleaching slurries and liquids, textile bleaching liquids and clay slurries.

\* \* \* \* \*